(12) United States Patent
Bhattacharyya et al.

(10) Patent No.: US 9,034,659 B2
(45) Date of Patent: May 19, 2015

(54) BIOSENSORS

(75) Inventors: Dhiman Bhattacharyya, Arlington, MA (US); Karen K. Gleason, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 228 days.

(21) Appl. No.: 13/548,521

(22) Filed: Jul. 13, 2012

(65) Prior Publication Data

US 2014/0193925 A1    Jul. 10, 2014

Related U.S. Application Data

(60) Provisional application No. 61/522,486, filed on Aug. 11, 2011.

(51) Int. Cl.
*G01N 33/543* (2006.01)
*G01N 27/327* (2006.01)
*G01N 33/531* (2006.01)

(52) U.S. Cl.
CPC ...... *G01N 33/54366* (2013.01); *G01N 27/3275* (2013.01); *G01N 33/54306* (2013.01); *G01N 33/531* (2013.01)

(58) Field of Classification Search
CPC ............ G01N 33/54366; G01N 27/3275; G01N 33/54306; G01N 33/5438; G01N 33/531
See application file for complete search history.

(56) References Cited

U.S. PATENT DOCUMENTS

| 7,618,680 | B2 | 11/2009 | Gleason et al. | 427/248.1 |
| 2002/0081587 | A1* | 6/2002 | Hwang et al. | 435/6 |
| 2006/0148066 | A1* | 7/2006 | Senecal et al. | 435/287.2 |
| 2009/0117268 | A1* | 5/2009 | Lewis et al. | 427/205 |
| 2010/0270180 | A1* | 10/2010 | Liu et al. | 205/794.5 |

OTHER PUBLICATIONS

Vaddiraju et al., Novel strategies for the deposition of-COOH functionalized conducting copolymer films and the assembly of inorganic nanoparticles on conducting polymer platforms, 2008, Advanced Functional Materials, vol. 18, pp. 1929-1938.*
A. Malinauskas, "Chemical deposition of conducting polymers," Polymer 42(9), 3957-3972 (2001).
D. Lin-Vien, et al., in *The Handbook of Infrared and Raman Characteristic Frequencies of Organic Molecules*; Academic Press: New York, 1991.
Dhiman Bhattacharyya et al., "High Surface Area Flexible Chemiresistive Biosensor by Oxidative Chemical Vapor Deposition," *Advanced Functional Materials*, vol. 21, No. 22, Nov. 22, 2011, pp. 4328-4337.
Shannon K. McGraw, "Antibody Immobilization on Conductive Polymer Coated Nonwoven Fibers for Biosensors," *Sensors & Transducers*, Dec. 28, 2011, XP55037130.
Dhiman Bhattacharyya et al., "Single-Step Oxidative Chemical Vapor Deposition of-COOH Functional Conducting Copolymer and Immobilization of Biomolecule for Sensor Application," *Chemistry of Materials*, vol. 23, No. 10, May 24, 2011, pp. 2600-2605.

(Continued)

*Primary Examiner* — Melanie Y Brown
(74) *Attorney, Agent, or Firm* — Steptoe & Johnson LLP

(57) ABSTRACT

A chemiresistive biosensor for detecting an analyte can include a high specific surface area substrate conformally coated with a conductive polymer, and a binding reagent immobilized on the conductive polymer, wherein the binding reagent has a specific affinity for the analyte. The conductive polymer can be deposited on a substrate by oCVD.

10 Claims, 8 Drawing Sheets

(56) References Cited

OTHER PUBLICATIONS

Baxamusa et al., "Initiated and oxidative chemical vapour deposition: a scalable method for conformal and functional polymer films on real substrates," *Physical Chemistry Chemical Physics, Royal Society of Chemistry*, vol. 11, No. 26, Jan. 1, 2009, pp. 5227-5240.

D Bhattacharyya et al., "Synthesis of Conducting Functional Copolymer by Oxidative Chemical Vapor Deposition (oCVD) and Its Sensor Application," Abstracts MRS Meeting 2010, Nov. 30, 2010, XP55037312; retrieved from URL: http://www.mrs.org/f10-abstract-hh/.

Senecal A et al., "Development of functional nanofibrous membrane assemblies towards biological sensing," *Reactive & Functional Polymers*, vol. 68, No. 10, Oct. 1, 2008, pp. 1429-1434.

* cited by examiner

BIOSENSORS

STATEMENT OF PRIORITY

This application claims priority to U.S. Provisional Application No. 61/522,486, filed on Aug. 11, 2011, which is incorporated by reference in its entirety.

STATEMENT REGARDING FEDERALLY SPONSORED RESEARCH OR DEVELOPMENT

This invention was made with government support under Grant No. W911NF-07-D-0004 awarded by the Army Research Office. The government has certain rights in this invention.

TECHNICAL FIELD

The present invention generally relates to biosensors and methods of making and using them.

BACKGROUND

Food and waterborne pathogens cause a considerable amount of disease all over the world. The Centers for Disease Control and Prevention estimated that around 76 million cases of foodborne diseases occur in the USA, resulting in 325,000 hospitalizations and 5000 deaths occur each year. Billions of dollars are lost due to bacterial contamination in foods and a similar amount of money is spent for related health care costs. Some foodborne diseases are well recognized, but are considered emerging because they have recently become more common. Among the various pathogens that can cause food borne illness, *Campylobacter, Salmonella, Listeria monocytogenes*, and *Escherichia coli* O157:H7 have been generally found to be responsible for majority of food-borne outbreaks.

Conventional food screening for detecting bio-threat risks and the toxins in the food supply can involve many steps, high labor and reagent costs, and be time consuming (e.g., minimum 2-3 days to obtain reliable information). Current biosensors can also suffer from user non-compliance because of the heavy weight of the sensor modules, and inflexibility of the sensor platforms for routine uses.

SUMMARY

Chemiresistive biosensors based on conductive polymers are described. The conductive polymers can be arranged on a high surface area substrate, such as a high surface area electro-spun polymer fiber mat. Such nanostructured fiber mats can be conformally coated by a conductive polymer, e.g., using oxidative chemical vapor deposition (oCVD). The oCVD polymer process is compatible with low-cost roll-to-roll manufacture. Functional groups in the conductive polymers can be further derivatized to immobilize analyte-specific binding reagents thus providing selectivity in detection of analytes. A wide variety of analytes can be detected by the biosensor, including pathogens.

In one aspect, a chemiresistive biosensor is configured to detect an analyte, and includes a high specific surface area substrate conformally coated with a conductive polymer, and a binding reagent immobilized on the conductive polymer, wherein the binding reagent has a specific affinity for the analyte.

The substrate can include an electro-spun polymer fiber mat. The substrate (e.g., the electro-spun polymer fiber mat) can have a BET surface area of at least 5 m²/g.

The conductive polymer can be a copolymer including the monomer units -[A]-, -[B]-, and -[B*]-; where A, B, and B* are distinct monomers; a homopolymer of monomer A is a highly conductive polymer; monomer B includes a reactive functional group selected to form a covalent link to a binding reagent; and monomer B* is monomer B covalently linked to the binding reagent.

The copolymer can have formula (I):

$$-[A]_x\text{-}[B]_y\text{-}[B^*]_z- \quad\quad (I)$$

where x, y, and z are the mole fractions of monomer A, B, and B* in the copolymer, respectively; and $0<x<1$, $0\leq y<1$, $0<z<1$, and $x>y+z$.

Monomer A and monomer B, independently, each can be an optionally substituted aniline monomer, an optionally substituted pyrrole monomer, or an optionally substituted thiophene monomer. Monomer A can be an EDOT monomer. Monomer B can be a 3-TE monomer or a TAA monomer. The binding reagent can be a protein.

In another aspect, a chemiresistive biosensor is configured to detect an analyte, and includes a high specific surface area substrate conformally coated with a conductive polymer; and a binding reagent immobilized on the conductive polymer, where the binding reagent has a specific affinity for the analyte; where the conductive polymer is a copolymer including the monomer units -[A]-, -[B]-, and -[B*]-; where A, B, and B* are distinct monomers; a homopolymer of monomer A is a highly conductive polymer; monomer B includes a reactive functional group selected to form a covalent link to a binding reagent; and monomer B* is monomer B covalently linked to the binding reagent.

In another aspect, a sensor array includes a plurality of sensor elements, where each sensor element includes a chemiresistive biosensor, and where each sensor element is configured to detect a different analyte.

In another aspect, a method of detecting an analyte includes contacting a sample suspected of containing the analyte with a chemiresistive biosensor which includes a high specific surface area substrate conformally coated with a conductive polymer; and a binding reagent immobilized on the conductive polymer; where the binding reagent has a specific affinity for the analyte.

In another aspect, a method of detecting a plurality of analytes includes contacting a sample suspected of containing at least one of the plurality of analytes with a sensor array including a plurality of sensor elements, where each sensor element includes a chemiresistive biosensor, and where each sensor element is configured to detect a different analyte.

In another aspect, a method of making a sensor configured to detect an analyte includes providing a high specific surface area substrate; coating a conductive polymer conformally on the high specific surface area substrate; and covalently linking a binding reagent to the conductive polymer, where the binding reagent has a specific affinity for the analyte.

Coating can include contacting the substrate with a vapor including an oxidant, a first monomer A, and a distinct second monomer B; where a homopolymer of monomer A is a highly conductive polymer; and monomer B includes a reactive functional group selected to form a covalent link to a binding reagent.

Covalently linking can include contacting the conductive polymer with the binding reagent and, optionally, a crosslink-

DETAILED DESCRIPTION

In general, chemiresistive biosensor detects the changes in resistance when analyte molecules specifically bind to the sensor surfaces. See, for example, J. Wei, B. Wu, *Sensors and Actuators, B: Chemical* 2009, B139, 429, which is incorporated by reference in its entirety. Chemiresistive biosensors can be attractive because they do not require labels (e.g., fluorescently labeled reagents); can provide faster detection than other techniques (such as PCR or ELISA); and can avoid the need for heavy instruments, such as SPR. See, for example, Alocilja E C, Radke S M. *Biosens Bioelectron.* 2003, 18, 841; and U. Lange, V. M. Mirsky, *Analytica Chimica Acta* 2011, 687, 105; each of which is incorporated by reference in its entirety. Chemiresistive biosensors can be rapid, portable, selective, highly sensitive, and stable.

Conducting polymers can be advantageously used in chemiresistive biosensors because of their mechanical flexibility, tunable conductivity, sensitivity, and room temperature operation, and low cost. See, e.g., U. Lange, V. M. Mirsky, *Analytica Chimica Acta* 2011, 687, 105; which is incorporated by reference in its entirety. Binding reagents (e.g., molecules which specifically bind a desired analyte) can be linked to a conducting polymer via a reactive functional group incorporated in the polymer, as illustrated in FIG. 1A.

Figure 1A:
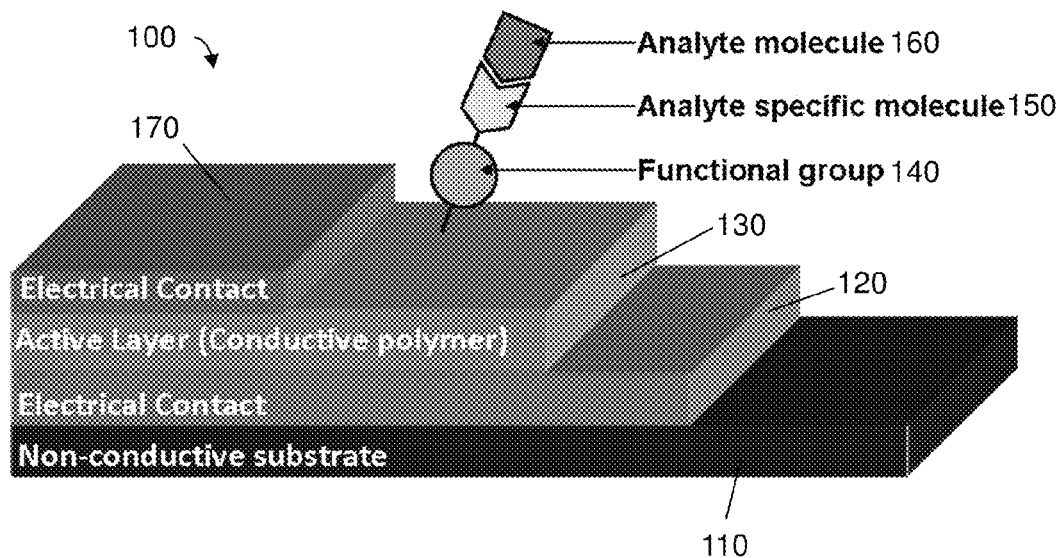
FIGS. 1A-1B are a schematic illustrations of chemiresistive biosensor devices.

FIG. 1A illustrates sensor 100 which includes a non-conductive substrate 110, upon which a first electrical contact 120 is arranged. A conductive polymer 130 is in electrical communication with first electrical contact 120. Functional group 140 is linked both to the conductive polymer 130 and to analyte specific molecule (i.e., binding reagent) 150. FIG. 1A illustrates the device in operation with an analyte molecule 160 bound to the analyte specific molecule 150. It is understood that the device as provided will generally not have analyte molecule 160 bound to the analyte specific molecule 150. Conductive polymer 130 is also in electrical communication with second electrical contact 170. The electrical resistance measured between first electrical contact 120 and second electrical contact 170 can undergo a change when the device is contacted with a sample containing analyte molecule 160 and analyte molecule 160 binds to analyte specific molecule 150. (Components for measuring the resistance are not shown in FIG. 1A). Because analyte specific molecule 150 does not bind substantially to other analytes which may be present in the sample, the device response is specific to the presence of the particular analyte molecule 160 for which analyte specific molecule 150 has a specific affinity.

Figure 1B:
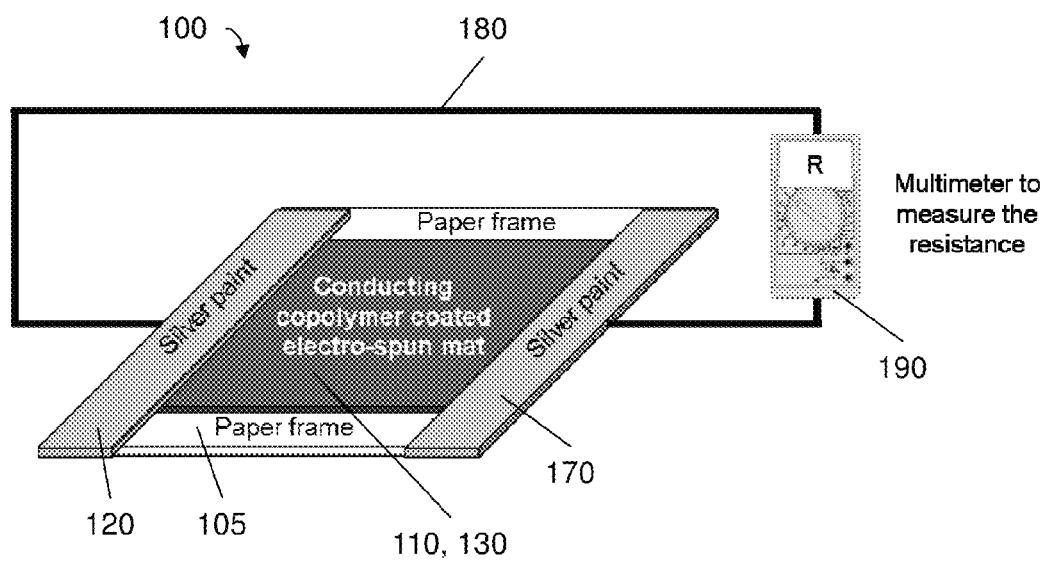

FIG. 1B illustrates an alternate configuration of device 100. In FIG. 1B, the non-conductive substrate 110 (e.g., an electro-spun fiber mat) has been coated with a conductive polymer 130. Although not shown in detail, in the configuration of FIG. 1B, the conductive polymer 130 is coated directly on non-conductive substrate 110; unlike the configuration of FIG. 1A, electrical contact 120 is not interposed between the substrate and the conductive polymer. Coated substrate 110, 130 is supported in frame 105. Although not shown in detail in FIG. 1B, the device includes functional group 140 which is linked both to the conductive polymer 130 and to analyte specific molecule (i.e., binding reagent) 150. Opposing edges of coated substrate 110, 130 are in electrical communication with first electrical contact 120 and second electrical contact 170. FIG. 1B shows that contacts 120 and 170 are connected via leads 180 to meter 190. Meter 190 can measure the resistance between contacts 120 and 170. As discussed above, that resistance can undergo a change when the device is contacted with a sample containing analyte molecule 160 and analyte molecule 160 binds to analyte specific molecule 150.

Figure 1C:
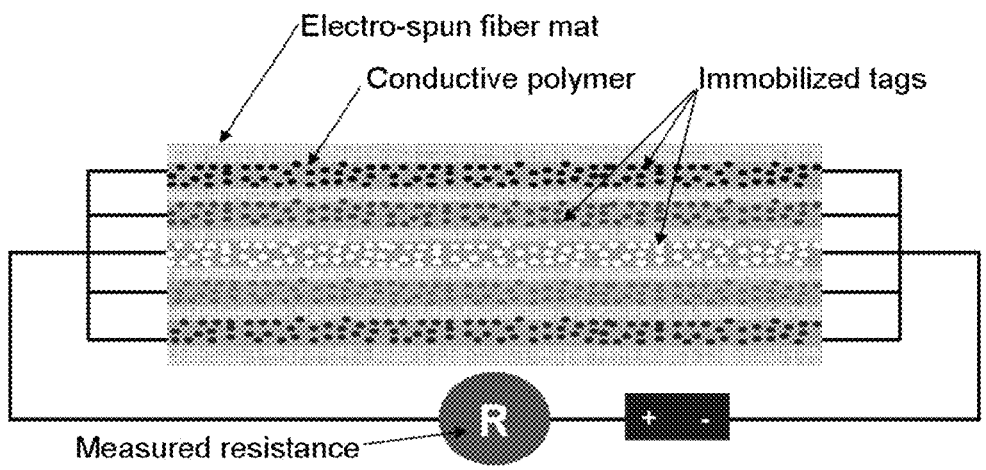
FIG. 1C schematically illustrates a chemiresistive biosensor array configured to detect more than one type of pathogens in a single device.
Figure 2:
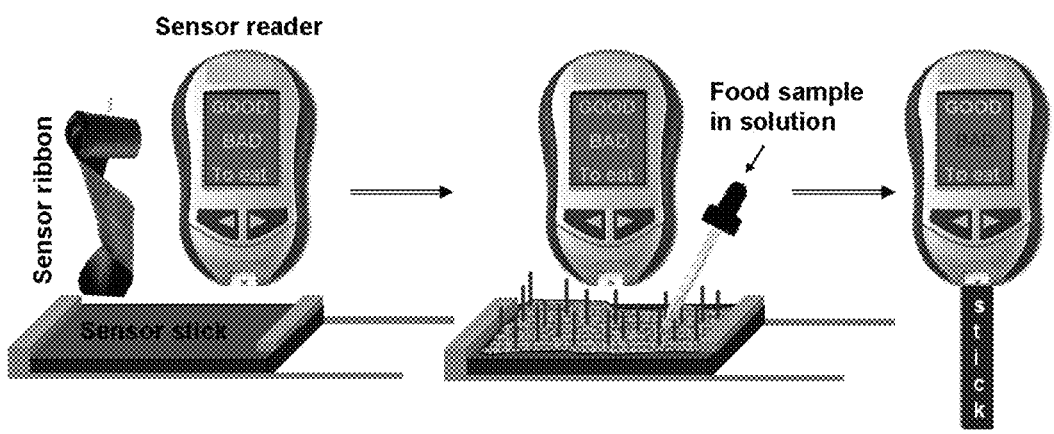
FIG. 2 schematically illustrates a hand-held food pathogen detecting sensor. It has a sensor ribbon including a high surface area electro-spun fiber mat, a sensor clip (stick) to attach the ribbons with the working electrodes, and a sensor reader to monitor the output.

Patterning the substrate, with regions having different binding reagents can provide a biosensor that can detect more than one different analyte on a single test strip. Patterning can be achieved, for example, by shadow masking. FIG. 1C illustrates such a device, in which a single substrate (in the illustration, shown as an electro-spun fiber mat) is patterned with multiple parallel regions. The regions each have a conductive polymer, and each has a different binding reagent (labeled as tags in FIG. 1C) immobilized on the conductive polymer, such that each region on the substrate can be measured individually for its response to its corresponding analyte. The substrate can be provided in the form of a test strip configured to be used with a testing device. The device can have separate electrical connections for each of the different strips, so that a single testing device can be used with a variety of different test strips.

For example, test strips can be provided that are configured for detecting multiple food-borne pathogens. The different regions of such a test strip could be used to test for the presence different pathogens, e.g., *E. coli, Campylobacter, Salmonella*, and *Listeria*, on a single test strip, using a single sample, and effectively simultaneously. Test strips can be provided that are configured for detecting multiple toxins, e.g., ricin, and lipopolysaccharides, on a single test strip, using a single sample, and effectively simultaneously. Because the test strips can be modular, test strips configured for different purposes can be used with the same testing device. The testing device provides electrical connections and necessarily electronics for measuring changes in resistance. The test strips can be inserted and removed from the testing device as needed.

A substrate can be coated with a conductive polymer. The conductive polymer can include conjugated bonds, such as conjugated aromatic groups; as such, monomer units of conductive polymers can include aromatic groups. Categories of monomers useful in conductive polymers include anilines, pyrroles, or thiophenes. For example, EDOT is a substituted thiophene monomer, such that a poly(EDOT) polymer is said to include EDOT monomer units. See FIG. 3. A conductive polymer can be a copolymer. Thus, monomer units of a conductive polymer can include an optionally substituted aniline, an optionally substituted pyrrole, an optionally substituted thiophene, or a combination of these. The conductive polymer can optionally include other monomer units as well.

One or more monomer units of the conductive polymer can include a reactive functional groups. Reactive functional groups include, for example, hydroxy, thio, amino, carboxyl, azide, or others. The reactive group can be pendant from the polymer backbone. Examples of monomer units including reactive functional groups include thiophene-3-acetic acid (TAA) or 3-thiopheneethanol (3-TE). A conductive polymer (copolymer) can include some monomer units with and some monomer units without a reactive functional group. Thus, in one example, the conductive polymer can be copolymer of e.g., EDOT and 3-TE monomers. The conductive polymer can be coated on the substrate by oCVD polymerization. In one example, the conductive polymer can be made by oCVD copolymerization of EDOT and 3-TE. The substrate can be an electro-spun polymer fiber mat.

The conductive polymer can be a copolymer including the monomer units -[A]- and -[B]-, and optionally additional monomer units. In other words, the conductive polymer can be made by copolymerization of monomer A and monomer B. In making the copolymer, one of the monomers, e.g., monomer A, can be chosen for its conductive properties. Monomer A can be chosen because a homopolymer of monomer A (i.e., poly(A)) is a highly conductive polymer. A "highly conductive polymer" is a conductive polymer that has a conductivity of at least 0.1 S/cm, 1 S/cm, at least 10 S/cm, at least 100 S/cm, or greater, on a given substrate. In some cases, monomer A may lack a reactive functional group. Monomer B can be chosen for the presence of a suitable reactive functional group. In some cases, a homopolymer of monomer B (i.e., poly(B)) is a conductive polymer (including a highly conductive polymer); in other cases, a homopolymer of monomer B can be a substantially nonconductive polymer.

For a given substrate and method of deposition, when monomer A has a conductive or highly conductive homopolymer, and monomer B has a less conductive or substantially nonconductive homopolymer, a copolymer of A and B can be a conductive polymer. The relative amounts of monomer units in the copolymer (e.g., of A, B, and other optional monomer units) can be selected to provide a balance between conductivity of the copolymer and the fraction of monomer units which provide reactive functional groups.

After copolymerization, the polymer can be further modified, e.g., by reaction of a reagent with a reactive functional group. The reactive functional group can be reacted with a complementary reactive functional group on a binding reagent. Reaction of two complementary reactive functional groups can result in a covalent bond between the conductive polymer and the binding reagent. For example, proteins can be linked to the hydroxyl group of 3-TE, the —NH— group of a pyrrole moiety (as in poly(pyrrole)), to the —COOH group of a thiophene-3-acetic acid moiety (as in poly (thiophene-3-acetic acid) or copolymers of thiophene-3-acetic acid with other conducting monomers), or to —N$_3$ groups of azide-functionalized conducting polymers. See, for example, F. S. Marrikar, et al., *Langmuir* 2007, 23, 1530; C. Malitesta, et al., *Thin Solid Films* 2010, 518, 3705; T. Kuwahara, et al., *Polymer* 2005, 46, 8091; and S-C. Luo, et al., *Langmuir* 2008, 24, 8071; each of which is incorporated by reference in its entirety. The binding reagent can have a specific affinity for a predetermined analyte.

In some circumstance, the binding reagent can be covalently linked to the conductive polymer via a crosslinking reagent. A crosslinking reagent can be useful when the reactive functional group on the conductive polymer does not react directly with a functional group on the binding reagent. A crosslinking reagent can provide a first reactive functional group which reacts with the reactive functional group of the conductive polymer, and can provide a second reactive functional group which reacts with a functional group on the binding reagent. In such a case, the crosslinking reagent can become incorporated into the final conductive polymer; the binding reagent is covalently linked to the conductive polymer (even though there is no covalent bond directly between an atom of the binding reagent and an atom of the conductive polymer). See, for example, FIG. 7.

The binding reagent can be any compound that has a specific binding affinity for a binding partner (i.e., the analyte). The binding reagent can be, e.g., a protein, an antibody, a peptide, a nucleic acid, a polysaccharide, or a small molecule (e.g., a metabolite or a drug). In some embodiments, the binding reagent is selected for its specific affinity to an analyte that is indicative of the presence of a biological entity (e.g., an organism, cells, or products thereof). Thus the sensor can detect the presence of, for example, a microorganism, in a sample. The sensor can also detect the presence of analytes that indicate a microorganism was at least at some point present in the sample (e.g., by detecting products that the microorganism can leave behind). In some embodiments, the binding reagent can be a protein or antibody.

Thus, a conductive polymer can have the formula:

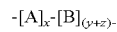

where A and B are distinct monomers; a homopolymer of monomer A is a highly conductive polymer and monomer B includes a reactive functional group; x and (y+z) represent the mole fractions of monomers A and B in the conductive polymer, respectively. After reaction with a binding reagent (and, optionally, a crosslinking reagent that facilitates the reaction between the reactive functional group and the binding reagent), the conductive polymer can have formula (I):

$$-[A]_x-[B]_y-[B^*]_z- \quad (I)$$

where monomer B* is monomer B covalently linked to a binding reagent, wherein x, y, and z are the mole fractions of monomer A, B, and B* in the copolymer, respectively; and 0<x<1, 0≤y<1, 0<z<1, and x>y+z.

In this example, (y+z) represent the mole fraction of monomer B in the initial copolymer; y represents the mole fraction of unreacted monomer B in the final polymer; and z represents the mole fraction of B* (i.e., covalently modified monomer B) in the final polymer. The final polymer is a conductive polymer, and can be a highly conductive polymer.

The substrate can preferably have a high specific surface area. In general, a fiber-based material provides a substantially higher specific surface area than a flat (i.e., smooth, non-textured) substrate. Therefore, we can extend this concept of making device on other substrates like, various types of papers, textile fibers, high surface area polymer nano-architectures.

The substrate can have an effective surface area greater than area the substrate occupies. The substrate can have a surface area that is greater than 1.5 times, greater than 2 times, greater than 5 times, greater than 10 times, greater than 25 times, greater than 50 times, greater than 100 times, or greater than 500 times the area the substrate occupies. In other words, the substrate can be a high specific surface area material.

The substrate can have a texture. For example, the texture can be fibrous, porous, granulated, patterned, ridged, stippled, corrugated, perforated, milled, or brushed. The substrate can include more than one texture, or a texture can be present on only a portion of the substrate. The substrate can be flexible, e.g., easily bent, folded or creased. A flexible substrate can be brittle or non-brittle.

The substrate can be a fibrous substrate, for example, paper or fabric. A fibrous substrate can include fibers, threads or filaments. Paper can be a felted sheet of fibers deposited on a screen from a water suspension. Examples of paper can include rice paper, tracing paper, tissue paper, toilet paper, bathroom tissue, facial tissue, newspaper, wax paper, paper currency, banana paper, inkjet paper, wallpaper, sandpaper, cotton paper, construction paper, book paper, printer paper, parchment, fish paper, TYVEK™, wove paper, buckypaper, or paper towels. Paper can be made from a number of materials including plant fibers, for example, fibers from wood, cotton, rice, wheat, bark, bamboo, hemp, or papyrus. Paper can also be made from materials including carbon, graphene oxide, or plastic. Products of any of these materials, or combinations of any of these materials can also be used to form paper.

Fabric can be a material made by weaving, felting or knitting natural or synthetic fibers or filaments. A fabric can also be made by electro-spinning synthetic fibers, to provide, e.g., an electro-spun fiber mat. A fabric can be made from natural materials, which can include for example, from carbon, cotton, silk, fleece, fur, leather, angora, mohair, alpaca wool, satin, goat wool, horse hair, flax, camel hair, cashmere, vicuna fleece, llama wool, milk proteins, grass, hemp, rush, straw, bamboo or wood. The fabrics made from natural sources can include linen, taffeta, tweed, wool, silk, canvas, cheesecloth, gauze, corduroy, denim, moleskin, poplin, sacking, terry cloth, lyocell, or velvet. Minerals, such as asbestos or basalt, can be used to make fabrics. Fabrics can be made from glass or metals, such as gold, silver, titanium, aluminum, copper or steel. A fabric can be synthetic, for example, satin, rayon, acrylic, acetate, nylon, aramid, latex, polyester, spandex, chiffon, polyvinyl chloride, sateen, olefin, ingeo, lurex, tulle, or viscose. A fabric can be a blend of natural materials, synthetic materials, or both.

The substrate can also be porous, meaning it can include pores or holes. A porous material can include, for example, plastic, sponge, ceramic, wood, clay, carbon or silicon. The substrate can be flexible, e.g., easily bent, folded or creased. A flexible substrate can be brittle or non-brittle.

As used herein "detecting" an analyte includes identification of the presence (and/or the amount and/or concentration) of the analyte in a sample. "Detecting" also includes the identification of the absence of the analyte in a sample. Identifying that an analyte is absent from a sample can include determining that if the analyte is present in a sample, it is present in an amount and/or concentration that is less than the lower limit of detection for that analyte for the sensor in question.

The biosensor can detect, for example, pathogens, toxins, other bioagents, or biomarkers. Pathogens that can be detected by the biosensor include *E. coli*, *Staphylococcus*, *Listeria*, *Salmonella*, *Campylobacter*, *Legionella*, Plague (*Yersinia pestis*), Tularemia (*Francisella tularensis*), or smallpox (variola major). Toxins that can be detected by the biosensor include ricin, Botulinum toxins (e.g., botulium toxin A, B, C1, C2, D, E, or F), anthrax, Subtilase cytotoxin, *Pasteurella multocida*, *Vibrio* RTX, *Helicobacter pylori* toxins, *Staphylococcus* toxins, cyanobacteria toxins, fungal ribotoxins, mycotoxins, cholera toxin, alpha Toxin, neurotoxins, α-, β-, or γ-bungarotoxin, caeruleotoxin, cereolysin, *Clostridium difficile* enterotoxin A, *Clostridium difficile* cytotoxin B, toxins from *Clostridium perfringens* (including lecithinase, kappa toxin, perfringolysin O, enterotoxin, beta toxin, delta toxin, or epsilon toxin), crotoxin, diphtheria toxin, listeriolysin, leucocidin, modeccin, nematocyst toxins, notexin, pertussis toxin, pneumolysin, *Pseudomonas aeruginosa* toxin A, saxitoxin, shigatoxin, *Shigella dysenteriae* neurotoxin, streptolysin O, *Staphylococcus* enterotoxin B or F, streptolysin S, taipoxin, tetanus toxin, viscumin, volkensin, or *Yersinia pestis* murine toxin. Further dangerous bioagents that can be detected by the biosensor include brucellosis (*Brucella* species), glanders (*Burkholderia mallei*), melioidosis (*Burkholderia pseudomallei*), psittacosis (*Chlamydia psittaci*), Q fever (*Coxiella burnetii*), or typhus fever (*Rickettsia prowazekii*).

The biosensor can be configured to detect biomarkers, e.g., compounds that are markers for disease or other conditions. Suitable biomarkers include: bone or cartilage degradation products; proteolytic enzymes; lipids or apolipoproteins; markers of inflammation; eicosanoids; markers of vascular function; markers of coagulation or fibrinolysis; hormones; markers of oxidative stress; markers of nutritional status; markers of satiety or satiation; amino acids; metals; and endogenous compounds or metabolites.

More specifically, suitable biomarkers include:

Acetaldehyde (=ethanal), Acetate, Acetoacetyl-CoA, Acetoin, Acetone, Acetyl-CoA, O-Acetyl-L-serine, N-Acetyl-D-mannosamine=2-Actamido-2-deoxy-D-mannose, Acetylphosphate, 2-Actamido-2-deoxy-D-mannose=N-Acetyl-D-mannosamine, ACTH, ADAMTS-1, ADAMTS-4, ADAMTS-5, Adenine, Adenosine, Adenosine 5'-phosphosulfate=Adenylylsulfate=APS, Adenosine diphosphoglucose (=ADPglucose), Adenosine-5'-diphosphate (ADP), Adenosine-5'-monophosphate (AMP), Adenosine-5'-triphosphate (ATP), Adenylosuccinate=N6-(1,2-Dicarboxyethyl)-AMP, Adiponectin, Agmatine=(4-Aminobutyl)guanidine, Aldosterone, Allantoate, Allantoin, Alpha,alpha-Trehalose, Alpha-D-Glucose (alpha-D-Glucopyranose), Alpha-D-Glucose 1-phosphate, Alpha-D-Glucose 6-phosphate, Alpha-Ketohydrocinnamicacid, Alzheimer secretase/BACE, Amino Acid profile, 3-Amino-1,2-propanediol (=1-Amino-2,3-propanediol), 1-Amino-2-propanol (=threamine=isopropanolamine), 2-Amino-6-hydroxypurine, 4-Aminobenzoic acid (=p-aminobenzoic acid=PABA), 4-Aminobutanal (=gamma-aminobutanal), (4-Aminobutyl)guanidine (agmatine), 4-Aminobutyricacid (=γ-amino-butyric acid=GABA), 5-Aminolevulinic acid, Anthrax Lethal Factor, Anti II a activity, Anti Xa activity, Antibrombin, APC resistance (APTT, global), APC resistance (APTT, specific), APC resistance (extrinsic, chromogen), Apo A-I, Apo A-II, Apo B-100, Apo E, Apo E-pheno-/genotyping, Apo's A1, B100, Lp(a), APTT, Arbutin, Arsenic, Ascorbic acid (Vitamin C), Beta thromboglobulin (urine/plasma), Beta-D-Fructose (=beta-D-Arabino-hexulose=beta-D-fructofuranose=D-Fructose=D-(−)-Fructose=D-Levulose=Fructofuranose), Beta-D-Fructose 6-phosphate, Beta-D-Fructose 1-phosphate, Beta-D-Glucose, Beta-D-Glucose 1-phosphate, Beta-D-Glucose 6-phosphate, Bicyclo-PGE, Bile acid profile, Bile acids, Biotin, Bombesin, (R,R)-2,3-Butanediol, (S,S)-2,3-Butanediol, Butanedionicacid, n-Butylamine, C4-b binding protein, C2C 5, C1, C2, Cadaverine (=1,5-Pentanediamine), Cadmium, Calcitonin, Carbamide, 3-Carboxy-3-hydroxy-4-methylpentanoate, 6-Carboxyhexanoate, Carotenoids, Cathepsin K, Cathepsin L, Cathepsin S, Cathepsin V, CCK, CD40-Ligand, Cellobiose, Cephalin=3-Phosphatidyl)-ethanolamine, Chitosamine (=D-Glucosamine=2-Amino-2-deoxy-D-glucose), Cholecystokinin (CCK), Cholesterol, Cholesterol-ester, β-Human Chorionic Gonadotropin (β-HCG), Chromium, Cis-Aconitic acid, Citrate, CoA-SH (Coenzyme A), Cobalt, COMP, Copper, Corticosterone, Cortisol, COX-1, COX-2, C-peptide, CPII, C-reactive protein (ultra-low), Creatinine, Crotonoyl-CoA, Crotonyl-CoA, CTx, Cytidine, Cytidine 5'-diphosphate (CMP), Cytidine 5'-diphosphate (CDP), Cytidine 5'-triphosphate (CTP), Cytosine, D4,7aketo PGF1a, D-Biotin, D-dimer, Decanoyl-CoA, 11-dehydro-TXB2, Density, 5'-Deoxy-5'-(methylthio)adenosine, 2'-Deoxyadenosine, 2'-Deoxyadenosine 5'-monophosphate (dAMP), 2'-Deoxyadenosine 5'-triphosphate (dATP), 2-Deoxy-beta-D-erythro-pentose, 2'-Deoxycytidine, 2'-Deoxycytidine 5'-diphosphate (dCDP), 2'-Deoxycytidine 5'-monophosphate (dCMP), 2'-Deoxycytidine 5'-triphosphate (dCTP), 2-Deoxy-D-ribose 1-phosphate, 2-Deoxy-D-ribose 5-phosphate, 2'-Deoxyguanosine, 2'-Deoxyguanosine 5'-diphosphate (dGDP), 2'-Deoxyguanosine 5'-monophosphate (dGMP), 2'-Deoxyguanosine 5'-triphosphate (dGTP), Deoxythymidine, 2'-Deoxythymidine 5'-phosphate (dTMP), 2-Deoxyuridine, 2'-Deoxyuridine 5'-phosphate (dUMP), 2'-Deoxyuridine 5'-triphosphate (dUTP), Dephospho-CoA, D-Erythrose 4-phosphate, D-fructose 1,6-bisphosphate, D-Galactose, D-Glucaric acid, D-Gluco-hexonic acid, D-Gluconic acid, D-Glucosaccharic acid (=d-Saccharic acid), D-Glucosamine 6-phosphate, D-Glyceraldehyde (=propanal, 2,3 dihydroxy), D-Glyceraldehyde-3-phosphate, D-Glycerate-2-phosphate (=2-phosphoglyceric acid), D-Glycerate-3-phosphate (=3-phosphoglyceric acid), 13,14-dihydro-15-keto-PGF, Dihydrofolate, Dihydroneopterin, (S)-4,5-Dihydroorotate, Dihydropteridine, 1,25-dihydroxy vitamin D, 1,25-dihydroxy vitamin D, 24,25-dihydroxy vitamin D, 24,25-dihydroxy vitamin D, 1,3-Dihydroxyacetone, Dihydroxyacetonephosphate=DHAP=Glyceronephosphate, 2,3-Dihydroxybenzoicacid, Dinor-6-keto-PGF1a, Dinor-TXB2, Diphosphate, D-Lyxulose, D-Mannitol, D-Mannitol 1-phosphate, D-Mannose (=carubinose), D-Mannose 6-phosphate, D-Ribose, D-Ribose 5-phosphate, D-Ribulose=D-Riboketose=D-Arabinoketose, D-Ribulose 5-phosphate, D-Tagatose (=lyxo-hexulose), dTDP, dTDP-D-glucose, dTTP, D-Xylose, D-Xylulose, Elastase degradation products of fibrin, Endothelin-1, 846 epitope, Estradiol, Ethanedioicacid, Ethylenesuccinicacid, Factor VII mass, Factor VIIa, Factor VIIc, Factor VIIIc, Factor X antigen, Factor XIIa, Faecessterols, Fatty acid profile, Fibrin degradation products (FbDP), Fibrinogen (clotting), Fibrinogen degradation products (FgDP), Fibrinogen (antigen), t-Fibronectin, Flavin adenine dinucleotide (FAD), Flavin mononucleotide (FMN=Riboflavin 5'-phosphate), Flavonoids, Folate, Folate, Follicle Stimulating Hormone (FSH), Formate (=Methanoic acid), Fragment 1+2, Free fatty acid, Free fatty acid, Free fatty acid profile (C14-C24), Free fatty acid profile (C14-C24), Free Thyroxine (FT4), Fumarate, 1-beta-D-Galactopyranosyl-4-alpha-D-glucopyranose, GCP-2, Ghrelin, Ghrelin (total or active), GLP-1, Glucagon, Glucagon-like peptide 1 (GLP-1), Gluconicacidlactone, Gluconiclactone, 1-alpha-D-glucopyranosyl-2-beta-D-fructofuranoside, 1-alpha-D-Glucopyranosyl-4-alpha-D-glucopyranose, Glucose, Glucuronic acid, Glutathione reduced (gamma-L-Glutamyl-L-cysteinyl-glycine), Glutathoine oxidized, Glycated Albumin, Glycated LDL, (R)-Glyceric acid, Glycerol, sn-Glycerol-3-phosphate, Glyc-HP, Glycine, ? 1-Glycoprotein, Glyoxylate, Granzyme B, Guanine, Guanosine, Guanosine 5'-diphosphate (GDP), Guanosine 5'-monophosphate (GMP), Guanosine 5'-triphosphate (GTP), HbA1c, HDL-cholesterol, HDL-cholesterol direct, Heptest, Hexanoyl-CoA, Homocystine, HP (PYD), Human Chorionic Gonadotropin (HCG), Human Growth hormone, 25-hydroxy vitamin D, 25-hydroxy vitamin D, 2-Hydroxy-1,2,3-propanetricarboxylicacid, 8-hydroxy-dG, Hydroxyproline, 1-Hydroxypropane-1,2,3-tricarboxylicacid, Hypoxanthine (=Purine-6-ol), IFN-gamma, IGF-1, I-kappaB, I-kappaB, 5'-Inosinate=5'-Inosine monophosphate, Inosine, Inosine 5'-diphosphate (IDP), Inosine 5'-monophosphate (IMP, inosinic acid), Inosine 5'-triphosphate (ITP), 5'-Inosine monophosphate=5'-Inosinate, Inositol (=myo-inositol=cyclohexitol), Insulin, Insulin, Insuline (IRI), Intact soluble fibrin, Interleukin-10, Interleukin-12, Interleukin-18, Interleukin-1β, Interleukin-4, Interleukin-6, Interleukin-8, Isocitrate, Isomaltose (=brachiose), Isopropanolamine=threamine=1-Amino-2-propanol, 2-Isopropylmalicacid, 8-isoprostane metabolites, Kallikrein generation test, 2-Keto-3-methylbutyricacid, 2-Ketobutyric acid=(2-Oxobutyricacid), keto-Phenylpyruvate, 2-Ketovaline, L(−)-5-Formyl-5,6,7,8-tetrahydrofolicacid (Folinic acid), (S)-Lactate, Lactose, L-Alanine, L-Arabinose, L-Asparagine, L-Aspartic acid, Lauroyl-CoA (=dodecanoyl-CoA), L-Cystathionine, L-Cysteine, L-Dicysteine, (V)LDL oxidation parameters, LDL particle size, LDL receptor genotyping, Lead, Leptin, Leptin, L-Glutamate, L-Glutamine, L-Histidine, L-Homocysteine, L-Homoserine, Lipid sep. after B.&Dyer ext., Lipid sep. after Folch ext., Lipids complete, Lipoamide, Lipoprotein separation, L-Isoleucine, LL-2,6-Diaminoheptane-dioic acid (=LL-2,6-Diaminopimelic acid), L-Leucine, L-Lysine, L-Methionine, L-Ornithine, LP (DPD), LP composition, Lp(a), L-Phenylalanine, L-Proline, LPS-induced TNF-alfa production in blood, L-Serine (=L-3-Hydroxy-alanine), LTB, LTC, LTE, L-Threonine, L-Tryptophan, L-Tyrosine, Luteïnising hormone (LH), L-Valine, Lysine carboxylic acid, (S)-Malate, Malonyl-CoA, Maltose, Manganese, Mannose, (Alpha-) D-Mannose 1-phosphate, MBL/MASP, MCP-1, MDA, MDA, MDA-TBARS, Melibiose, Menaquinone (=Vitamin K2), Mercaptopyruvate, Mercapturic acids, Mercury, 3-Methyl-2-oxobutanoate, (S)-3-Methyl-2-oxopentanoate, 4-Methyl-2-oxopentanoate, 4-Methyl-5-(2'-hydroxyethyl)-thiazole, 3-Methylbut-2-enoyl-CoA (=3-methylcrotonyl-CoA), 3-methylcrotonyl-CoA=(3-Methylbut-2-enoyl-CoA), Methylsterols, 5-Methylthioadenosine, β-2 microglobulin (BMG), Minerals, MMP activity, MMP-1, MMP-1, MMP-13, MMP-13 gelatinase, MMP-14, MMP-2, MMP-3, MMP-3, MMP-8, MMP-9, Motilin, Myristoyl-CoA (=tetradecanoyl-CoA), N(alfa)-Acetyl-L-ornithine, N-Acetyl-D-glucosamine 1-phosphate, N-Acetyl-D-glucosamine 6-phosphate, N-Acetyl-L-glutamate, NAD (=beta-Nicotinamide adenine dinucleotide, oxidized), NADH (=beta-Nicotinamide adenine dinucleotide, reduced), NADP (=beta-Nicotinamide adenine dinucleotide 2-phosphate, (oxidized), NADPH (=beta-Nicotinamide adenine dinucleotide 2'-phosphate, (reduced), NF-kappaB, NF-kappaB, N-Formyl-L-methionine, Niacin, Nickel, Nicotinamide (=Niacinamide=Vit B3=Vit PP), Nicotinamide D-ribonucleotide, Nicotinate, Nicotinicacidamide, 3-nitro-tyrosin, 3-nitrotyrosine (free and/or total), NO, NOx, NOx, NTx, Octanoyl-CoA, Oestradiol (E2), Orotate, Orotidine-5'-monophosphate (Orotidylic acid), Orthophosphate, Osteocalcin (Bone GLA protein, BGP), Osteocalcin carboxylation degree, O-Succinyl-L-homoserine, Oxalic acid, 2-Oxobutanoicacid, 2-Oxobutyricacid (=2-Ketobutyric acid), Oxoglutaricacid, 2-Oxoisocaproate, 2-Oxopropanoicacid, t-PA activity, PA1-1antigen, PABA=4-Aminobenzoic acid (=p-aminobenzoic acid), PAI-1 activity, t-PA antigen, t-PA:PA1-1 complex, Palmitoyl-CoA (=hexadecanoyl-CoA), Pantothenic acid, (R)-Pantothenicacid, Pentosidine, Peroxides, PGD2, PGE2, PGE2, 11β-PGF, 6-keto PGF1a+2,3 dinor 6-Keto-PGF1a (urine), 6-keto-PGF1a, 8-iso-PGF2-alpha, 8-iso-PGF2-alpha (urine), PGF2a, 3-Phenyl-2-oxopropanoate, Phenylpyruvate, Phosphate, (3-Phosphatidyl)-ethanolamine (=cephalin), Phosphatidylglycerol=3-(3-sn-phosphatidyl)glycerol, 3'-Phosphoadenylylsulfate (PAPS), 6-Phospho-D-gluconate (=6-phosphogluconic acid), Phosphoenolpyruvate (PEP), 6-Phosphogluconic acid=(6-Phospho-D-gluconate), Phosphoglycolic acid, Phospholipids, Phytosterols/stanols, PICP, Pimelate, PINP, s-PLA2, Plasmin antiplasmin (PAP), Plasmin inhibitor, Plasminogen, Platelet factor 4, Porphobilinogen, Prephenic acid, Progesterone (Prog), Prokallikrein, Prolactin (PRL), Propanoic acid, Propanoyl-CoA (=Propionyl-CoA), Prostate Specific Antigen (PSA), Protein C activity, Protein C antigen, Protein carbonyls, Protein conc. Bradford, Protein conc. Lowry, Protein S activity, Protein S antigen, Prothrombin, Pseudouridine, PT (including INR), Pteroylglutamicacid, PTH, Putrescine (=1,4-Butanediamine=Tetramethylenediamine), 3-Pyridinecarboxylicacid, Pyridoxal, Pyridoxal-5-phosphate, Pyridoxine, Pyridoxol, Pyrophosphate, Pyroracemicacid, Pyruvate, PYY, PYY, RANTES, Renin, Resistin, Riboflavin (=lactoflavin=Vitamin B2), (9-D-Ribosylxanthine)-5'-phosphate, SAA, SAA, Saccharose, Salicin (=Salicoside), Scu-PA or u-PA antigen, Selenium, Selenomethionine, s-E-Selectin, Shikimic acid, s-ICAM, Soluble fibrin, Somatostatin, Sorbitol (=gulitol=glucitol), Spermidine (=N-(3-Aminopropyl)-1,4-butane-diamine), Spermine (=N,N'-Bis(3-aminopropyl)-1,4-butanediamine), Succinate, Succinyl-CoA, Sucrose 6-phosphate, TAFI antigen, Testosterone, 5,6,7,8-Tetrahydrofolate, Tetrahydrofolicacid, TFPI (free), TFPI (total), TGF-β2, TGF-β1, Thiamine-diphosphate, Thiaminemonophosphate, Threamine=isopropanolamine=1-Amino-2-propanol, Thrombin generation, Thrombin-antithrombin (TAT), s-Thrombomodulin, Thymidine, Thymidine 5'-diphosphate (TDP), Thymidine 5'-monophosphate (Thymidylic acid=TMP), Thymidine 5'-triphosphate (TTP), Thymidine-5'-monophosphate, Thyroid Stimulating Hormone (TSH), TNFa, TNFa converting enzyme (TACE/ADAM17), Total fatty acid profile (C8-C24), Total fatty acid profile (C8-C24), Total Homocystein, Total thyroxine (T4) (human), Trace elements, Trans-4-Hydroxy-L-proline, Trans-butenedioicacid, Trehalose 6-phosphate, Triglycerides, Triglycerides, Triiodothyronine (T3), TXA2+11-dehydro-TXB2 (urine), TXB2, UDP-D-galactose, UDP-D-glucose, UDP-N-acetyl-D-glucosamine, Undecaprenol, Uracil-6-carboxylicacid, Urate, Urea, Uridine, Uridine 5'-monophosphate (=uridylic acid=UMP), Uridine 5'-triphosphate (UTP), Urine=8-iso-PGF2-alpha, Urocanate, Vanadium, s-VCAM, Vitamin A, Vitamin B1, Vitamin B12, Vitamin B2, Vitamin B3, Vitamin B6, Vitamin C, Vitamin D 1,25-dihydroxy, Vitamin D 1,25-dihydroxy, Vitamin D 24,25-dihydroxy, Vitamin D 24,25-dihydroxy, Vitamin D 25-hydroxy, Vitamin D 25-hydroxy, Vitamin E, Vitamin K1, Vitamin K1, Vitamin K1, Von Willebrand factor, Xanthine, Xanthosine, Xanthosine 5'-monophosphate (=Xanthylicacid=XMP), or Zinc.

Nanostructured conductive polymeric platforms can enhance the sensitivity of biosensors. Binding reagents (e.g., proteins) have been immobilized to nanostructures such as nanorods, nanowires, or nanoribbons of conductive polymers. See, for example, J. A. Arter, et al., *Nano Lett.*, 2010, 10, 4858; K. Ramanathan, et al., *J. Am. Chem. Soc.*, 2005, 127, 496; and N. Chartuprayoon, et al., *J. Phys. Chem. C*, 2010, 114, 11103; each of which is incorporated by reference in its entirety. Such nanostructured materials can provide much higher specific surface area for immobilization of binding reagents than comparable substrates lacking the nanostructures (e.g., flat substrates). With a higher surface area at small scales, more binding reagents can be immobilized per unit of (macro-scale) area. With more binding reagents per unit area, the sensitivity of the sensors increases. However, conductive polymers nanostructures floating freely in suspension can be too delicate for regular use. In contrast, fabrics made of electro-spun (or e-spun) polymeric fibers provide high specific surface area substrates that are easily handled. Electro-spun fibers coated with a conformal functional conducting polymer film can make a flexible, highly sensitive chemiresistive biosensor.

Electro-spun nonwoven fiber mats can have a larger specific surface area and smaller pore size than commercial nonwoven textiles. Electro-spun fiber mats can have a specific surface area in the range of, for example, 1 to 100 m$^2$/g, 5 to 75 m$^2$/g, or 10 to 50 m$^2$/g, expressed as (for example) a BET surface area. Porosity can vary, e.g., from 25% to 80%, with a pore size in the range of, for example, 0.05 to 50 μm, 0.10 to 10 µm, or 0.15 to 5 µm. See, for example, *Environ. Sci. Technol.* 2005, 39, 7684-7691, and Y. J. Ryu et al., *European Polymer Journal* 39 2003, 1883-1889, each of which is incorporated by reference in its entirety. Fiber diameter can influence the properties (e.g., specific surface area or porosity), with mats made from smaller-diameter fibers having a higher specific surface area.

Electro-spun fiber mats can be made from different polymers, including but not limited to polymers such as nylon, polyacrylonitrile, polyethylene, or polycarbonate. Other polymer-based fiber mats can be used as a substrate in a biosensor.

Textured substrates, including, e.g., electro-spun fiber mats require conformal thin film deposition techniques to provide reproducible and uniform properties when surface coating with a conducting polymer. Traditional wet chemical procedures to synthesize and form thin films on a solid support can be difficult to execute on electro-spun fiber mats. Wet chemical methods can also be restricted by poor solubility of the polymers. See, e.g., J. P. Lock, et al., *Macromolecules* 2006, 39, 5326, which is incorporated by reference in its entirety. Electrochemical polymerization of conductive monomers is well established technique and has been extensively studied for the synthesis of various conductive polymers and copolymers. See, for example, C. Malitesta, et al., *Thin Solid Films* 2010, 518, 3705; and T. Kuwahara, et al., *Polymer* 2005, 46, 8091; each of which is incorporated by reference in its entirety. However, electrochemical synthesis is limited by the requirement that the substrate be conductive. In this regard, it should be noted that chemiresistive sensors measure the resistance changes of the conducting polymer upon exposure to the analytes; hence, a nonconductive substrate is required to begin with. The requirements of electrochemical synthesis can be incompatible with the requirements of a chemiresistive sensor.

Vapor phase deposition methods can produce thin films of insoluble and infusible materials, which describes most conducting polymers. Vapor deposition can avoid the use of heat and solvents, and therefore can be compatible with virtually any substrate, yet provide relatively more conformal deposition than other techniques. Among the vapor phase thin film deposition techniques for conducting polymer synthesis, vapor-phase polymerization (VPP) has become common. See, for example, P. A. Levermore, et al., *Adv. Mater.* 2007, 19, 2379; M. Fabretto, et al., *Polymer*, 2010, 51, 1737; J. Cho, et al., *Synthetic Metals* 2010, 160, 1119; D. O. Kim, et al., *Thin Solid Films* 2009, 517, 4156; and M. Fabretto, et al., *Macromolecular Rapid Communications* 2008, 29, 1403; each of which is incorporated by reference in its entirety. Thin film deposition of a conducting polymer by vapor-phase polymerization typically involves the application of a thin layer of oxidant solution (e.g., a ferric chloride solution) on the substrate, evaporation of the solvent, and exposure of the oxidant layer to monomer vapor under mild vacuum. VPP can coat e-spun fibers with conducting polymers. See, e.g., S. Nair, et al., *J. Mater. Chem.* 2008, 18, 5155; A. Laforgue, L. Robitaille, *Chem. Mater.* 2010, 22, 2474; and A. Laforgue, *J. Power Sources* 2011, 196, 559; each of which is incorporated by reference in its entirety.

Oxidative chemical vapor deposition (oCVD) is another technique for vapor phase thin film deposition of conducting polymers. In oCVD, a substrate is simultaneously exposed to an oxidant and monomer vapor, resulting in a uniform and conformal polymeric film on the substrate. Conducting polymers can be made by selecting appropriate monomers. Due to very low volatility, some of the monomers of conducting polymers can benefit from heating to obtain an operating vapor pressure in oCVD. Unlike VPP, oCVD does not require pretreatment of substrates with oxidant, which can damage the substrate. See, e.g., S. H. Baxamusa, et al., *Phys. Chem. Chem. Phys.* 2009, 11, 5227; which is incorporated by reference in its entirety.

The oCVD synthesis of homopolymer PEDOT can be achieved using oxidants such as ferric chloride, cupric chloride, or bromine. See, for example, J. P. Lock, et al., *Macromolecules* 2006, 39, 5326; S. G. Im, K. K. Gleason, *Macromolecules* 2007, 40, 6552; S. G. Im, et al., *App. Phys. Lett.* 2007, 90, 152112/1; S. G. Im, et al., *ACS Nano*, 2008, 2, 1959; and H. Chelawat, et al., *Chem. Mater.* 2010, 22, 2864; each of which is incorporated by reference in its entirety. Also, oCVD can copolymerize thiophene-3-acetic acid (TAA) with 3,4-ethylenedioxythiophene (EDOT) and pyrrole by using ferric chloride; and to copolymerize TAA and EDOT using bromine as a volatile oxidant. See, for example, S. Vaddiraju, et al., *Adv. Func. Mater.* 2008, 18, 1929; S. Vaddiraju, K. K. Gleason, *Nanotechnology* 2010, 21, 125503/1; D. Bhattacharyya, K. K. Gleason, *Chem. Mater.* (Published online on Apr. 26, 2011 as Article ASAP), DOI: 10.1021/cm2002397; each of which is incorporated by reference in its entirety. The —COOH groups of TAA monomers were retained in the copolymer and used to covalently attach nanoparticles or protein molecules. Since the vapor pressure of TAA is very low compared to EDOT, copolymerization was very slow and yielded a low fraction of TAA in the random copolymer. The conductivity of these copolymers can ranges from 0.1 S/cm to 10 S/cm. Polymers with higher conductivity can be preferred to improve the signal to noise ratio (and therefore sensitivity) in a biosensor. See, e.g., K. Sugiyasu, T. M. Swager, *Bull. Chem. Soc. Japan* 2007, 80, 2074, which is incorporated by reference in its entirety.

Chemical vapor deposition (CVD) processes can form thin films of electrically active polymers. (See, for example, U.S. Pat. No. 7,618,680 and references cited therein, each of which is incorporated by reference in its entirety.) CVD techniques can make PEDOT that has a conductivity over 4 S/cm and can be spectroscopically comparable to commercial product deposited from the solution phase. This technique can be applicable to other oxidatively polymerized conducting materials like polypyrrole, polyaniline, polythiophene, or their substituted derivatives. Side reactions stemming from acid generation during oxidative polymerization can lead to bond breakage in the monomer and the formation of unconjugated oligomers that can result in films with low conductivities. These unwanted reactions can be minimized via three different methods: introducing pyridine as a base, heating the substrate (e.g., the surface to be coated), and applying a bias to the sample stage.

Conducting polymer materials can be formed via oxidative polymerization of aniline, pyrrole, thiophene, or their derivatives. (A. Malinauskas, "Chemical deposition of conducting polymers," Polymer 42(9), 3957-3972 (2001), which is incorporated by reference in its entirety). In general, it has not been feasible to process bulk material of these polymers into thin films since they can be insoluble and non-melting, but coating techniques have been developed on substrates including plastic, glass, metal, fabric or micro- or nano-particles. Four main approaches can be utilized to form coatings of anilines, pyrroles, or thiophenes via oxidative polymerization on various materials: electropolymerization of monomers at electrodes, casting a solution of monomer and oxidant on a surface and allowing the solvent to evaporate, immersing a substrate in a solution of monomer and oxidant during polymerization, and chemical oxidation of a monomer directly on a substrate surface that has been enriched with an oxidant.

CVD can be an all-dry process for depositing thin films of conducting polymers that are currently available on the market only as solution-based materials. The absence of the acidity associated with solution-based films can reduce corrosion of neighboring layers that can cause early device failure. Moderate stage temperatures and vapor phase coating can allow depositing conducting films on a wide range of unconventional organic and inorganic high surface-area materials, including paper, fabric, and small particles. CVD can be a significant tool for organic semiconductor manufacturers seeking capabilities to incorporate conducting polymers in all-dry fabrication processes.

EXAMPLES

Figure 3:
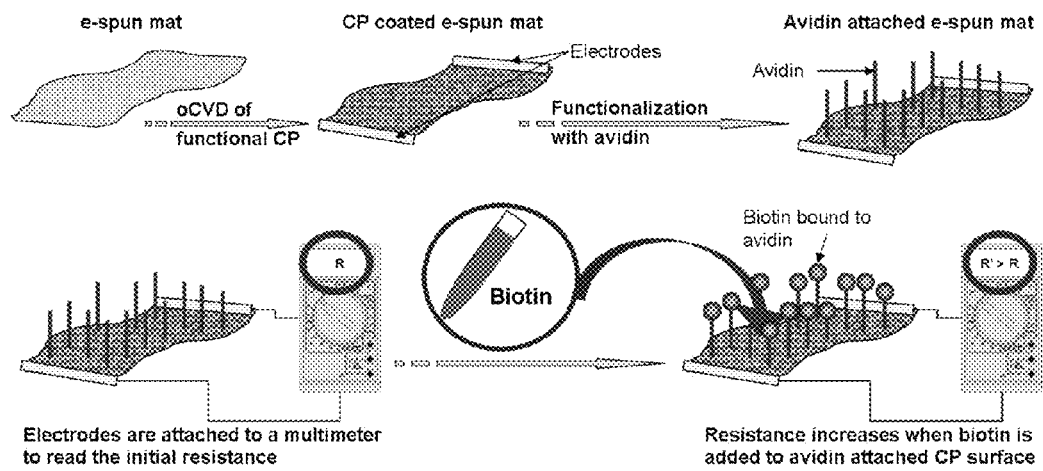
FIG. 3 is a schematic presentation of the fabrication steps of a chemiresistive biosensor which includes an electro-spun polymer fiber mat.

As described in detail below, a highly conductive copolymer bearing hydroxyl functional groups was synthesized by copolymerizing 3,4-ethylenedioxythiophene (EDOT) and 3-thiopheneethanol (3-TE) by oCVD. Ferric chloride was used as the oxidant. The copolymer thin films deposited on electro-spun fiber mats were characterized by FT-IR, UV-Vis and X-ray photoelectron spectroscopies, scanning electron microscopy and conductivity measurements. The hydroxyl functional groups were used for covalent immobilization of a biomolecule (avidin) and the resulting structure was tested for its sensing abilities against micro-molar to nano-molar concentrations of biotin in aqueous solution. FIG. 3 illustrates the method of making a biosensor which is described below. The flexible electro-spun fiber mats provided a specific surface area many times higher than corresponding flat substrates. Thus, the response and the response time of the biosensor were significantly improved.

Materials. 3,4-Ethylenedioxythiophene (97%), 3-thiopheneethanol (98%) and iron (III) chloride (reagent grade) were purchased from Sigma-Aldrich, St. Louis, Mo. The monomers and iron chloride were used as received. Dichloromethane and BSA (Bovine serum albumin) was obtained from Sigma-Aldrich, St. Louis, Mo. as well. PBS buffer, pH 7.4 (phosphate buffered saline), avidin, biotin and PMPI (p-maleimidophenylisocyanate) were purchased from Pierce Biotechnology, Rockford, Ill.

Preparation of electro-spun fiber mat. Nylon nano fibers were made by using a 13% solution of 50/50 glacial acetic and formic acids. The solution was then put into the Nanospider (El Marco, Czech Republic) with the following conditions: A 5 wire mandrel was rotated through the solution at 20 rpms voltage was set at 50 kV. The fibers were drawn upwards toward the grounded collector for 15 minutes. The fibrous mat was then removed and used in the oCVD coating process.

Oxidative chemical vapor deposition of poly(EDOT-co-3TE). To deposit homopolymers of EDOT or 3TE monomers, the corresponding monomer vapor was delivered to the reactor from a side-port and procedures described elsewhere were followed. See S. G. Im, K. K. Gleason, *Macromolecules* 2007, 40, 6552; S. G. Im, et al., *App. Phys. Lett.* 2007, 90, 152112/1, each of which is incorporated by reference in its entirety. Briefly, monomer jar and feed lines were heated to 150° C. to avoid condensation and pressure drop in the reaction chamber. The substrate temperature was maintained at 80° C. by a temperature controlled stage.

The samples were placed upside down in the reactor chamber. Ferric chloride powder was placed in a stainless steel crucible and resistively heated to ~350° C. in order to provide ferric chloride vapor. Next, the valve of the monomer vapor was opened and the reaction was allowed to continue until the desired polymer thickness was obtained. The vapor pressure of the feed monomers was 150 mTorr and was controlled by a butterfly valve. For deposition of the copolymer of EDOT and 3TE monomers, a 1:1 mixture of the monomers was placed in the monomer jar and a similar deposition process was followed. Pure homopolymers, such as PEDOT and P3TE were deposited using ferric chloride to compare and correlate the spectroscopic and conductive properties of the copolymer. As-deposited conductive films were rinsed with methanol to remove any excess ferric chloride and then dried in air.

Covalent immobilization of avidin. A 0.5 mg/mL solution of PMPI was prepared in anhydrous dichloromethane. Copolymer coated electro-spun fiber mats were submerged in the PMPI solution overnight at room temperature. PMPI reacted fiber mats were washed with excess dichloromethane to remove any excess PMPI. The PMPI attached electro-spun mats were then submerged in a 2 mg/mL avidin solution in PBS buffer, pH 9.0, and allowed to react for 24 hours. Avidin reacted samples were then washed with excess PBS solution and finally with distilled deionized water.

Labeled avidin (FITC) attachment was done by cutting the fibrous mat into desired size and put into PMPI solution for one hour. The samples were then rinsed with PBS buffer to remove the unreacted PMPI then membrane was exposed to labeled avidin at 100 μg/mL and allowed to react for one hour. The fibrous membranes were then removed and rinsed with PBS and exposed to biotinylated Qdots (Invitrogen, Qdot 655 nm) in PBS overnight to the attached avidin activated membranes. The samples were then rinsed thoroughly in PBS and imaged.

Characterization. The initially produced oCVD films were analyzed by FTIR spectroscopy using a Nexus 870, Thermoelectron Corp. X-ray Photoelectron Spectroscopy (XPS) data for the polymeric films were done in a Surface Science instrument (SSI, Model: SSX-100) equipped with a monochromator and the data were analyzed in CasaXPS software. The thickness and conductivity of the films deposited on glass were measured by a KLA Tenchor P-16 surface profilometer and a four-point probe (Model: Keithley SCS-4200), respectively. Scanning electron micrographs were obtained by a tabletop Hitachi TM3000 microscope with acceleration voltage of 5 kV. The images of the fluorescence labeled avidin and quantum dot labeled biotin attachments to the fibers were obtained using a Zeiss LSM model 710 Laser Scanning Confocal Microscope.

Resistance measurements. Resistance values were obtained by connecting the chemiresistor devices with two alligator clips to a multimeter. Briefly, a 2 cm×2 cm piece of avidin-bound of electro-spun mat was submerged in a petri dish containing 10 mL of PBS buffer (pH 7.4) for 30 minutes with opposite sides being connected to a multimeter. Once a baseline resistance was obtained over 15 minutes, 10 mL of biotin solution of a given concentration was added to the petri dish and the resulting solution was stirred. The resistance values were noted at fixed time intervals for 15 minutes after addition of biotin solution.

Calculation of the Response and Response Time of the Devices.

Changes in the resistances of the avidin immobilized e-spun mats and flat substrates on exposure to biotin solutions were converted into responses ($R_p$) using the following relationship:

$$R_P(\%) = \left(\frac{R_1 - R_0}{R_0}\right)100 \qquad (1)$$

Here, $R_1$ is the resistance of the avidin immobilized e-spun mat after being exposed to biotin solution at any given time, $R_0$ is the resistance of the avidin immobilized e-spun mat. The response time is defined as the time required for the device to attain 1/e of the maximum response. See S. Vaddiraju, K. Seneca, K. K. Gleason, *Adv. Func. Mater.* 2008, 18, 1929; which is incorporated by reference in its entirety.

The experimentally obtained response data sets against time were used to fit a simple reversible binding kinetic model as described elsewhere (J. R. Wayment, J. M. Harris, *Anal. Chem.* 2009, 81, 336). Here biotin reacts with immobilized avidin molecules at a rate given by the product of the biotin concentration, C, and a second-order rate constant, $k_{bind}$, while the bound complex dissociates at a first-order rate, $k_{unbind}$. Therefore, the Equation 2 represents the rate of change in biotin-bound avidin fraction:

$$d\theta/dt = (1-\theta)k_{bind}C - \theta k_{unbind} \quad (2)$$

Solutions to this differential equation under the boundary conditions where $\theta=0$ at $t=0$ and $\theta$ was constant at $t>0$ provided the time dependence of the bound complex fraction on exposure to biotin solution of concentration, C.

$$\theta(t) = [k_{bind}C/(k_{bind}C+k_{unbind})][1-\exp(-(k_{bind}C+k_{unbind})t)] \quad (3)$$

This model assumed no changes in the solution concentration at the interface and diffusion limited time to resupply biotin molecules to the surface. Additionally and most importantly, it assumes that a single biotin-avidin binding event, which increases the $\theta$, results in a positive response. That means each single biotin-avidin binding reactions can be monitored by observing the resistance changes as a function of time. This assumption allowed $\theta$ to be replaced with $R_p(\%)$ in equation 3, giving:

$$R_p(\%)(t) = [k_{bind}C/(k_{bind}C+k_{unbind})][1-\exp(-(k_{bind}C+k_{unbind})t)] \quad (4)$$

Equation 4 was used to fit the experimental data by the least squares method.

Figure 4:
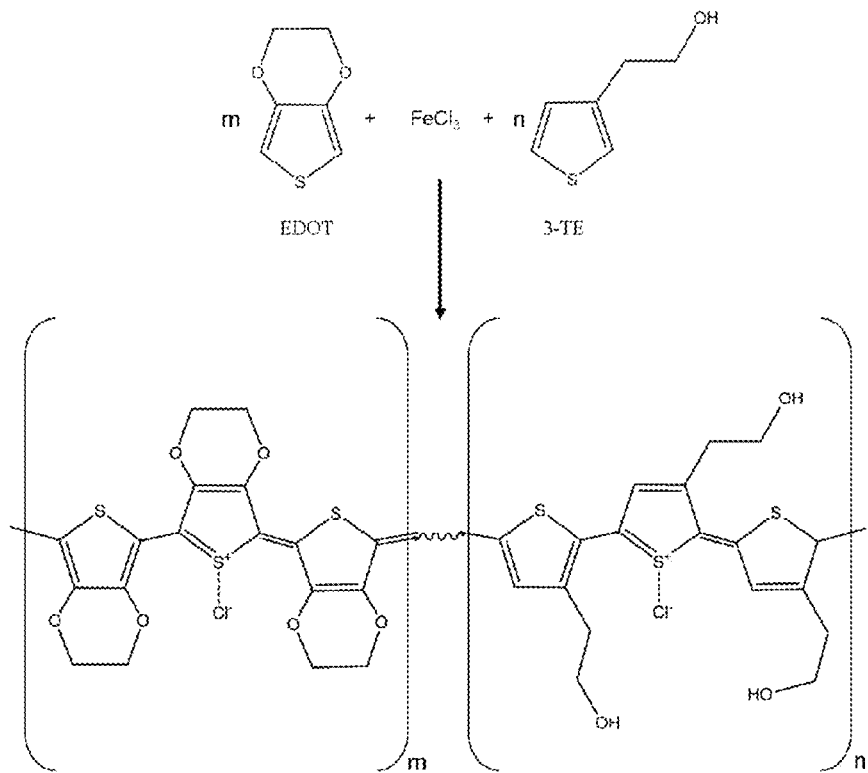
FIG. 4 illustrates the copolymerization of EDOT and 3TE using ferric chloride in an oCVD process. Chloride ions are present as dopant in the repeating units, but the number of dopants shown in FIG. 4 does not necessarily represent the actual dopant concentration.

Results and discussion. FIG. 4 depicts the structures EDOT and 3TE monomers, and the random copolymer synthesized by oCVD method using ferric chloride as oxidant. Polymerization of EDOT by oCVD using iron chloride provides very highly conductive polymer (see, e.g., S. G. Im, K. K. Gleason, *Macromolecules* 2007, 40, 6552; and S. G. Im, et al., *App. Phys. Lett.* 2007, 90, 152112/1; each of which is incorporated by reference in its entirety), however, pure PEDOT lacks any functional group than can be employed for immobilization of a biomolecule. On the other hand, polymers of 3-substituted thiophenes (without other comonomers) have poor conducting properties. Therefore, a copolymer of EDOT and 3TE was chosen to provide both good conductivity and allow for attachment of biomolecules.

Figure 5:
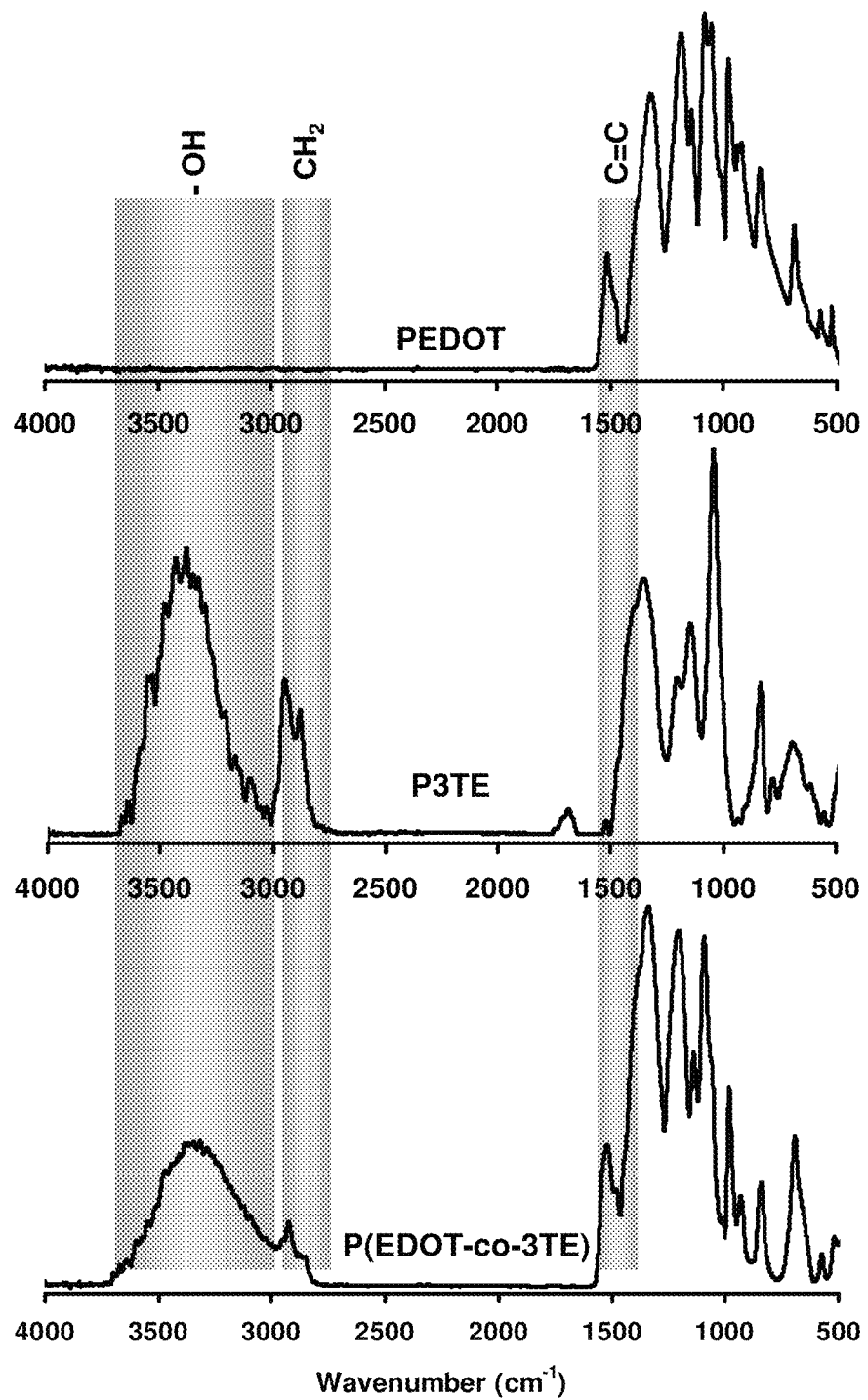
FIG. 5 shows FT-IR spectra of oCVD grown PEDOT, P3TE and P(EDOT-co-3TE) using iron (III) chloride as oxidant.

FIG. 5 shows the FT-IR spectra of PEDOT and poly(3TE) (also referred to as P3TE) separately, and of poly(EDOT-co-3TE) copolymer. Presence of a characteristic C=C peak at 1520 cm$^{-1}$ in PEDOT confirmed the conjugation in the polymeric system and as expected, no other peak is observed at higher wavenumbers (see, e.g., S. G. Im, K. K. Gleason, *Macromolecules* 2007, 40, 6552, which is incorporated by reference in its entirety). The FT-IR spectrum of P3TE showed a very low intensity C=C peak and a small peak near ~1700 cm$^{-1}$. This 1700 cm$^{-1}$ peak may have indicated the presence of >C=O groups in the polymer and it could be a result of the over-oxidation of hydroxyl groups. Presence of high intensity —OH peaks (~3400 cm$^{-1}$) and $CH_2$ peaks (2900 cm$^{-1}$) confirmed the retention of the side chain in the oCVD synthesized P3TE polymer. See, for example, D. Lin-Vien, et al., in *The Handbook of Infrared and Raman Characteristic Frequencies of Organic Molecules*; Academic Press: New York, 1991, which is incorporated by reference in its entirety. The FT-IR spectrum of the poly(EDOT-co-3TE) had all the characteristic peaks of the corresponding monomers. Presence of —OH peaks at ~3400 cm$^{-1}$ confirmed the retention of the functional groups in the copolymer. The possible over-oxidation of the hydroxyl groups by the oxidant was not observed in the copolymer. To ensure that the thin film obtained by oCVD method was not a mixture of the two monomers, the deposited film was rinsed with methanol and THF to remove any absorbed monomer molecules in the film.

The oCVD-grown PEDOT was highly conductive, as measured in a 4-point probe instrument. However, a homopolymer P3TE film was non-conductive. UV-Vis measurements showed that this P3TE film absorbed light from ~600 nm, which is a characteristic of non-conducting semiconductors. The conductivity of the copolymer was relatively higher than previously reported for other oCVD-synthesized copolymers. Without wishing to be bound by a particular theory, the conductivity of this random copolymer may arise from the EDOT monomer units, which would be consistent with the conductivity being less than for homopolymer PEDOT and more than for homopolymer P3TE, as shown in Table 1;

TABLE 1

Conductivity measurements of the deposited conductive polymers and copolymer

| Polymer/copolymer | Conductivity (S cm$^{-1}$) |
|---|---|
| PEDOT | 300 |
| P3TE | 0 |
| poly(EDOT-co-3TE) | 25 |

Figure 6:
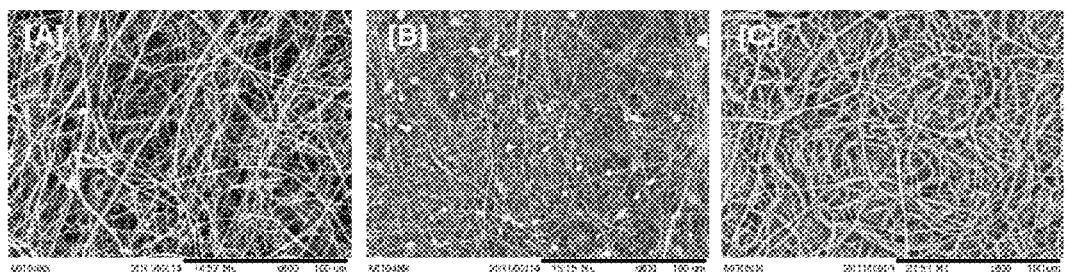
FIGS. 6A-6C show scanning electron microscopic images of the (FIG. 6A) as prepared electro-spun nylon mat, (FIG. 6B) conductive copolymer coated mat, and (FIG. 6C) avidin immobilized to the conductive copolymer coated mat. Scale bar, 100 μm.

The retention of the structural integrity of the electro-spun fiber mat substrate was verified at different points during sensor manufacture. Scanning electron microscopic (SEM) images were recorded of the fibers of electro-spun nylon mats as-prepared (FIG. 6A), after conformal deposition of the copolymer (FIG. 6B), and after conjugation of avidin to the functional groups (FIG. 6C). The SEM images confirmed that the fibrous structures of the mat were retained even after the avidin immobilization. The appearance of the copolymer-coated mat in FIG. 6B was different than uncoated or avidin attached mats. This difference might have originated from the variation in the fiber structures in the electro-spun fiber mats across different samples. Similar structures have been reported (see, e.g., S. Vaddiraju, K. Seneca, K. K. Gleason, *Adv. Func. Mater.* 2008, 18, 1929, which is incorporated by reference in its entirety).

That the fibrous structure was not disrupted by the processing meant that high specific surface area of the substrate was retained. Unlike other methods, such as solution or evaporative coating, the oCVD deposition produced conformal films. Solution coating can lead to aggregation of particulates in the fiber matrix without coating the fibers. Evaporation can produce a blanket layer over the entire mat, reducing the specific surface area of the mat (more like a flat substrate). In addition, neither solution nor evaporation gives high conductivity on electro-spun mats (see, e.g., S. Vaddiraju, K. Seneca, K. K. Gleason, *Adv. Func. Mater.* 2008, 18, 1929, which is incorporated by reference in its entirety).

Figure 7:
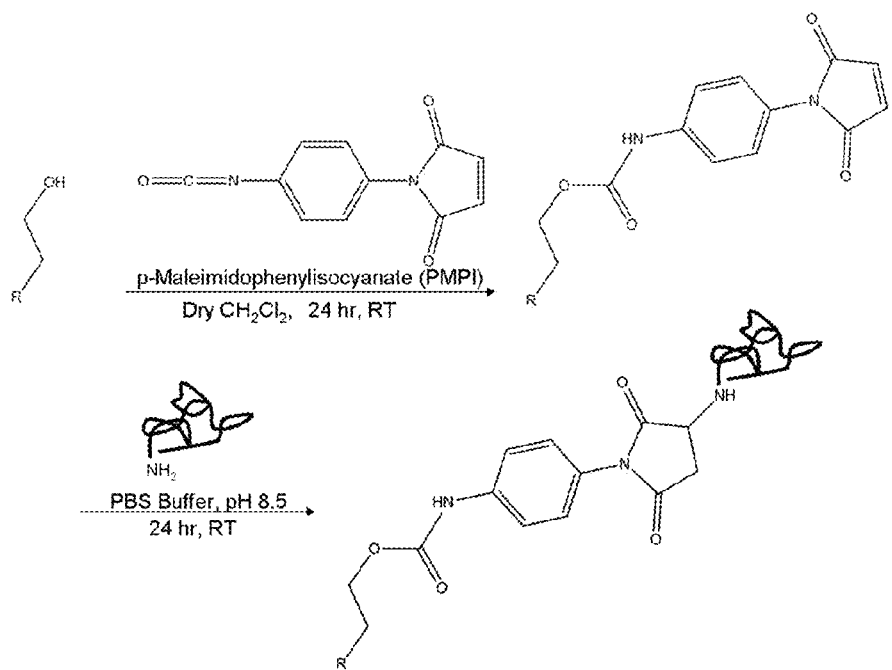
FIG. 7 illustrates covalent immobilization of protein molecules to the functional groups of the copolymer. R represents the rest of the copolymer chain.

Hydroxyl functional groups of the poly(EDOT-co-3TE) copolymer were reacted with a crosslinker molecule to attach biomolecules to the conductive polymer surface. In this particular case, p-maleimidophenylisocyanate (PMPI) was employed as the crosslinker. The active isocyanate (—N═C═O) groups were first allowed to react with the —OH groups of the polymer. Maleimido groups are commonly used to attach proteins by reaction with thiol groups of the protein. In this case, the maleimido groups were specifically reacted with protein —$NH_2$ groups at an elevated pH (pH>8.5). See G. T. Hermanson, in *Bioconjugate Techniques*; 2nd ed., Academic Press, USA 2008, p 183, which is incorporated by reference in its entirety. FIG. 7 illustrates the reaction steps as discussed above.

Figure 8:
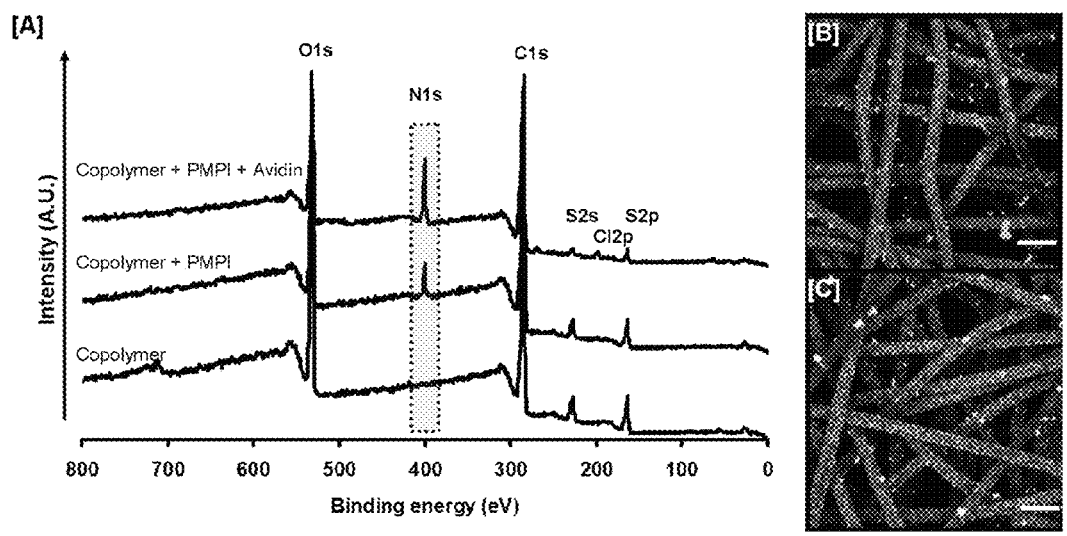
FIG. 8A shows X-ray photoelectron survey spectra of P(EDOT-co-3TE) copolymer, PMPI attached copolymer and avidin immobilized copolymer showing presence of O1s, C1s, S2s, S2p and Cl2p peaks. A step-wise increment in the atomic percent of nitrogen (N1s) was observed as highlighted in the box.
FIGS. 8B-8C are laser scanning confocal microscope images of the fibers after covalent attachment of FITC-avidin (green fluorescence) to the fibers, and reaction of biotinylated red quantum dots to the FITC-avidin on the fibers, respectively. Scale bar, 50 μm.

FIG. 8A shows X-ray photoelectron survey spectra of the conductive copolymer films at the different steps of the avidin immobilization process. XPS survey scans of the copolymer show the presence of C, O, and S as the characteristic elements of the comonomers. Chlorine was present as the dopant in the polymeric film. Appearance of the N1s peak in the copolymer after PMPI attachment confirmed that the reaction occurred between the —OH groups of the copolymer and the isocyanate groups of the PMPI crosslinker molecules. About 4% increase in the atomic concentration in the nitrogen content was solely due to the two nitrogen atoms present in each PMPI molecule. The atomic concentration of nitrogen increased to ~12% after avidin was linked to the surface. This 8% increase in the surface nitrogen concentration after avidin immobilization reflected the presence of attached avidin on the copolymer surface.

To further validate the covalent attachment of avidin to copolymer, FITC-avidin was covalently attached to the electro-spun fibers as shown in FIG. 8B. Green fluorescence of FITC-avidin on the fibers showed the conformal nature of the avidin bound to the fiber surfaces. Moreover, similar results were observed when biotinylated red-fluorescing quantum dots were allowed to bind to the FITC-avidin, as shown in FIG. 8C. An increase in the electrical resistance of the avidin bound mat was observed when biotin molecules was bound to the surface.

To evaluate how the chemiresistor devices responded to various concentrations of biotin, the sensor structure was exposed to solutions ranging from 5 nM to 5 μM biotin and the device resistance monitored over a span of 15 minutes.

Figure 9:
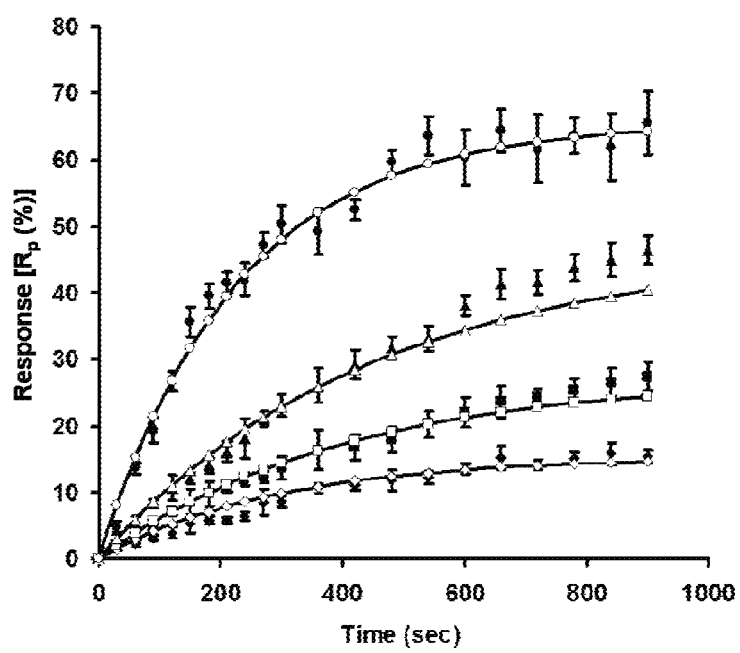
FIG. 9 is a graph showing the response [Rp(%)] of a biosensor device to varying concentrations of biotin: 5 nM (rhombus), 50 nM (square), 500 nM (triangle) and 5 μM (circles). The closed shapes represent experimental data; open shapes are the best fit data plotted with a solid line to show the trend. Error bars show the standard deviation of the experimental data.

FIG. 9 shows the responses of the sensor made on electro-spun mat as a function of time for different concentrations of biotin solutions. As expected, the response time was shorter at higher concentrations. The kinetics of the biotin-avidin reaction was modeled by fitting the experimentally obtained responses. Equation 4 provided the time dependency of the responses. Solving this equation, the binding ($k_{bind}$) and unbinding ($k_{unbind}$) rates of biotin and surface-bound avidin interactions were found to be $1.5\pm0.6\times10^7$ $M^{-1}s_{-1}$ and $3.3\pm0.4\times10^{-5}$ $s^{-1}$, respectively. The biotin-avidin affinity equilibrium constant, $K_a$, can be estimated from the ratio of $k_{bind}$ and $k_{unbind}$. In this case, $K_a = k_{bind}/k_{unbind} = 4.5\pm0.2\times10^{11}$ $M^{-1}$. This value is very close to the previously reported binding affinity values of $5.5\times10^{11}$ $M^{-1}$ (see J. R. Wayment, J. M. Harris, *Anal. Chem.* 2009, 81, 336; which is incorporated by reference in its entirety) and $3.71\times10^{11}$ $M^{-1}$ (see S. Zhao, W. M. Reichert, *Langmuir,* 1992, 8, 2785, which is incorporated by reference in its entirety), where binding affinities were evaluated for a similar system. However, the estimated $K_a$ values are ~4 orders of magnitude less than the avidin-biotin association constant of $1.6\times10^{15}$ $M^{-1}$ in solution phase (see N. M. Green, *Adv. Protein Chem.* 1975, 29, 85, which is incorporated by reference in its entirety). This difference in binding affinities may result from the combined influence of avidin surface density, avidin accessibility, surface crowding of avidin-bound biotin molecules. Additional influences, such as aggregation, protein conformational changes, non-ideal binding may also be responsible for this difference.

Figure 10:
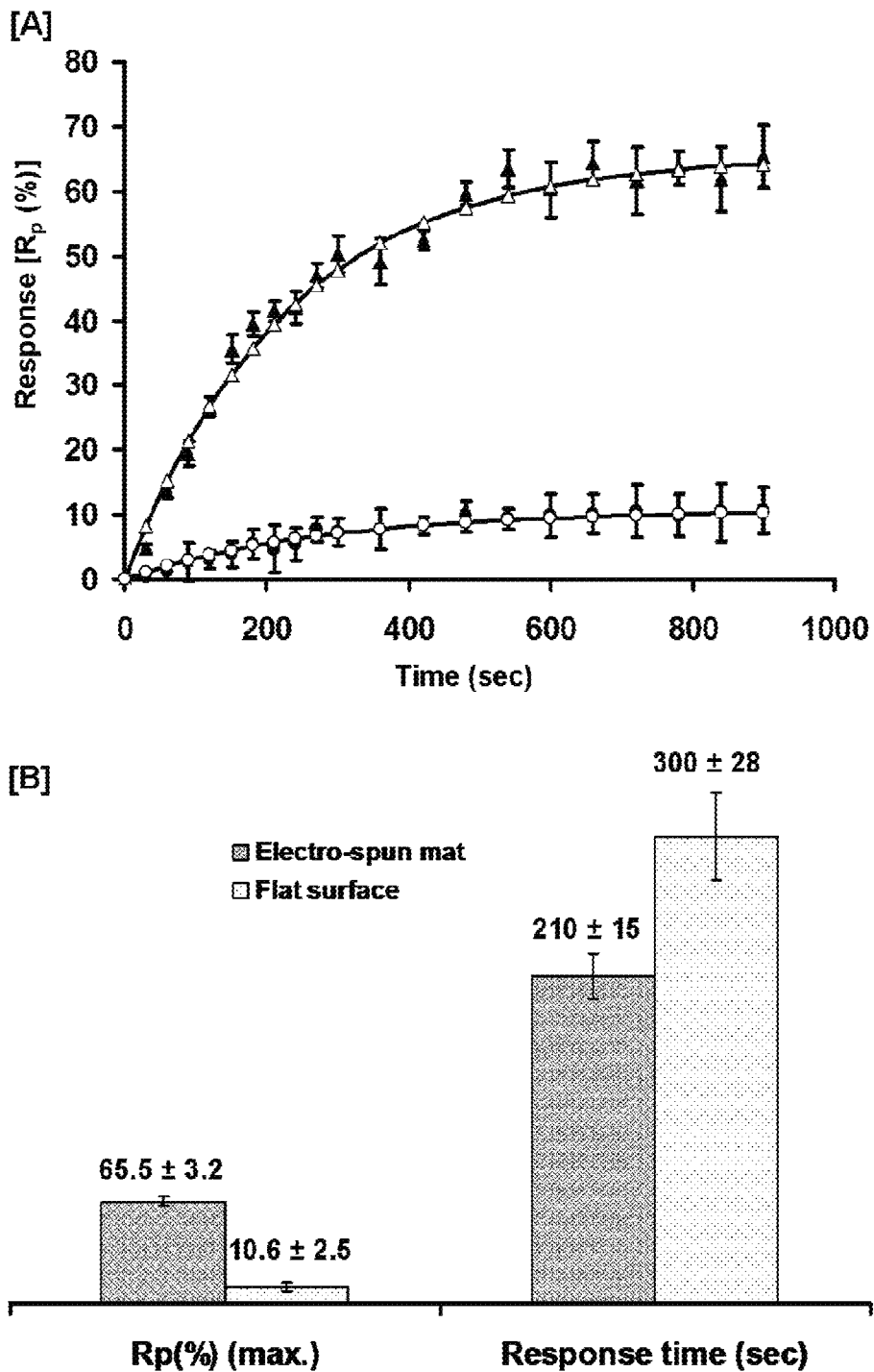
FIG. 10A is a comparison of the responses of devices made on an electro-spun mat (closed triangles) and a flat substrate (closed circles). The closed shapes represent experimental data; open shapes are the best fit data plotted with a solid line to show the trend.
FIG. 10B is a comparative chart of maximum response [Rp(%) (max.)] and the response time for devices made on an electro-spun mat or on a flat substrate.

FIG. 10A represents a comparison of the responses of avidin bound conductive copolymer chemiresistor devices made on electro-spun mat and a flat substrate (glass coverslip) when a 5 μM biotin solution was used as the analyte. Once the biotin solution was added to the buffer, the response for the flat substrates reached saturation ~10 minutes, whereas that for the electro-spun mat continued to increase and reached saturation at ~15 minutes. The maximum response obtained by the devices made on electro-spun mat was ~65% and ~10% for a flat substrate, as shown in FIGS. 10A-10B. Because the electro-spun mat had a much higher specific surface area than the flat glass substrate, it contained more analyte-binding sites (i.e. more avidin molecules linked to the surface).

Table 2 shows a comparison between two devices, one made as described above and the other with gold nanorod-modified electrodes as reported by Lee et al., *Biosen. & Bioelec.* 2008, 23, 1117, which is incorporated by reference in its entirety. The electrodeposited gold nanorods have much higher surface area than the electro-spun fiber mats due to the nanostructure and high aspect ratio of the nanorods. However, the metallic structure made the nanorod-based device brittle. Devices made on an electro-spun mat were highly flexible yet had a comparable detection limit.

TABLE 2

|  | Lee et al. | Current work |
| --- | --- | --- |
| Size | 1.2 mm × 1.2 mm | 2 cm × 2 cm |
| Structure | Electrodeposited gold nanorods | Conformal conductive copolymer coated electro-spun fiber mat |
| Substrate | Metallic-gold | Polymeric - conductive copolymer |
| Detection limit | 1 ng/mL concentration of biotin | ~1 nM concentration of biotin |
| Response time | Not reported | <4 minutes |

Figure 11:
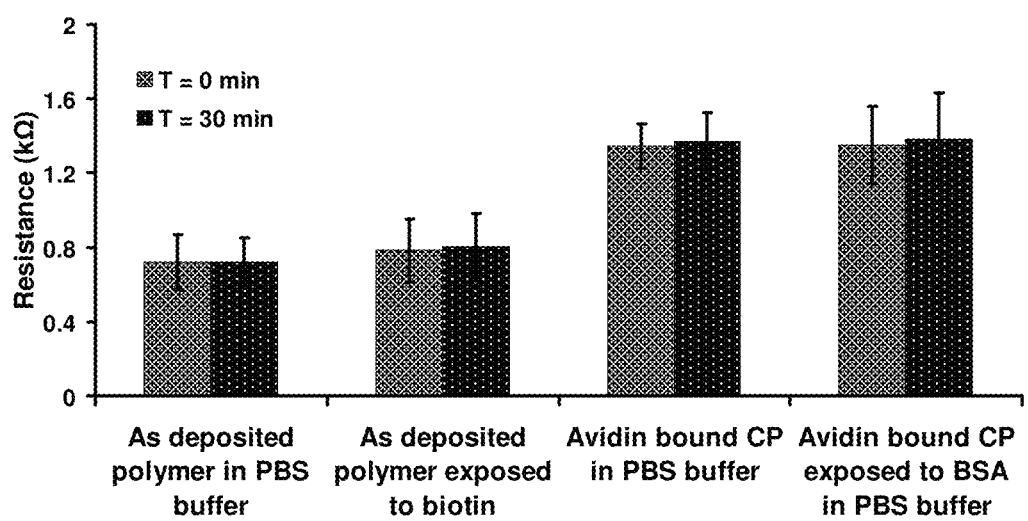
FIG. 11 shows resistance of the as-deposited copolymer and avidin-linked copolymer.

A biosensor is desirably specific and sensitive to its analyte. For that reason, avidin-bound chemiresistor devices were tested in a variety of control experiments. First, the effect of being submerged in buffer on resistance was measured. Diffusion of dopants into the buffer might be expected to affect resistance. The first column in FIG. 11 showed that an insignificant change (<2%) in resistance occurred when as-deposited copolymer was submerged in the buffer for 30 minutes. Avidin-bound copolymer showed similar results (third column in FIG. 11).

To test if the oCVD-grown copolymer itself adsorbs biotin from solution, the as-deposited copolymer was exposed to biotin solution for 30 minutes (second column in FIG. 11). No significant change in resistance (<2%) was observed.

To test analyte specificity, the avidin-bound conducting copolymer was exposed to a solution of bovine serum albumin (BSA) which was not expected to bind to avidin. As shown in the last column of FIG. 11, almost no change (<2.5%) in resistance was observed. This confirmed that only the specific analyte triggered the change in resistance.

Other embodiments are within the scope of the following claims.

What is claimed is:
1. A chemiresistive biosensor configured to detect an analyte comprising:
a high specific surface area substrate conformally coated with a conductive polymer;

a binding reagent immobilized on the conductive polymer, wherein the binding reagent has a specific affinity for the analyte; a first electrode, wherein the first electrode is in contact with one side of the conductive polymer; and a second electrode, wherein the second electrode is in contact with the opposite side of the conductive polymer.

2. The biosensor of claim 1, wherein the substrate includes an electro-spun polymer fiber mat.

3. The biosensor of claim 1, wherein the substrate has a BET surface area of at least 5 m$^2$/g.

4. The biosensor of claim 1, wherein the conductive polymer is a copolymer including the monomer units -[A]-, -[B]-, and -[B*]-; wherein A, B, and B* are distinct monomers; a homopolymer of monomer A is a highly conductive polymer; monomer B includes a reactive functional group selected to form a covalent link to a binding reagent; and monomer B* is monomer B covalently linked to the binding reagent.

5. The biosensor of claim 4, wherein the copolymer has formula (I):

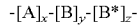  (I)

wherein x, y, and z are the mole fractions of monomer A, B, and B* in the copolymer, respectively; and
0<x<1,
0<y<1,
0<z<1, and
x>y+z.

6. The biosensor of claim 4, wherein monomer A and monomer B, independently, are each an optionally substituted aniline monomer, an optionally substituted pyrrole monomer, or an optionally substituted thiophene monomer.

7. The biosensor of claim 4, wherein monomer A is an EDOT monomer.

8. The biosensor of claim 4, wherein monomer B is a 3-TE monomer or a TAA monomer.

9. The biosensor of claim 1, wherein the binding reagent is a protein.

10. A sensor array comprising a plurality of sensor elements, wherein each sensor element includes a chemiresistive biosensor according to claim 1, and wherein each sensor element is configured to detect a different analyte.

* * * * *